United States Patent [19]

Nair et al.

[11] Patent Number: 5,891,881
[45] Date of Patent: Apr. 6, 1999

[54] AMINOHETEROCYCLE-SUBSTITUTED GLYCEROLS

[75] Inventors: Haridasan K. Nair, Williamsville, N.Y.; Andrew C. Peterson, Madison, Wis.

[73] Assignee: Clarion Pharmaceuticals Inc., Madison, Wis.

[21] Appl. No.: 976,408

[22] Filed: Nov. 21, 1997

[51] Int. Cl.[6] .......................... A61K 3/52; C07D 473/18; C07D 473/26; C07D 239/02; C07D 249/08; C07D 233/28

[52] U.S. Cl. .......................... 514/261; 514/262; 514/383; 514/398; 514/405; 514/407; 544/277; 544/332; 548/263.8; 548/330.1; 548/362.1; 548/372.5

[58] Field of Search .................................... 544/277, 317, 544/332; 514/258, 275, 261, 262, 398, 383, 405, 404; 424/443; 548/330.11, 263.8, 362.1, 312.5

[56] References Cited

U.S. PATENT DOCUMENTS

| | | | |
|---|---|---|---|
| 4,036,974 | 7/1977 | Walker et al. | 424/273 |
| 5,116,992 | 5/1992 | Braquet et al. | 514/77 |
| 5,252,575 | 10/1993 | Harnden et al. | 514/261 |
| 5,543,414 | 8/1996 | Nestor et al. | 514/262 |
| 5,641,783 | 6/1997 | Klein et al. | 514/263 |

FOREIGN PATENT DOCUMENTS

| | | | |
|---|---|---|---|
| 0157609A2 | 9/1985 | European Pat. Off. . | |
| 0452680 | 10/1991 | European Pat. Off. | 544/277 |
| 0564006 | 10/1993 | European Pat. Off. | 544/277 |

OTHER PUBLICATIONS

Ueda et al., Synthesis of N–(2,3–Dihydroxypropyl) Derivatives of Nucleic Bases, *J. Heterocycl. Chem.* (1971), 8: 827–829.

Hiller et al., Pyrimidine nucleoside analogues X. 5–substituted 1–(1,3–dihydroxypropyl–2) uracils, *Nucleic Acids Research* (1976), 3: 721–727.

Holy et al., Synthesis of New Mono– and Disubstituted Hydroxyalkyl and Aminoalkyl Derivatives of Heterocyclic Bases, *Collect. Czech. Chem. Comm.* (1978), 43: 3444–3465.

Holy et al., Acyclic Nucleotide Analogs Derived from 8–Azapurines: Synthesis and Antiviral Activity, *J. Med. Chem.* (1996), 39: 4073–4088.

DeClerq et al., (S)–9–(2,3–Dihydroxypropyl)adenine: An Aliphatic Nucleoside Analog with Broad–Spectrum Antiviral Activity, *Science* (1978), 200: 563–565.

DeClerq et al., A novel selective broad–spectrum anti–DNA virus agent, *Nature* (1986), 323: 464–467.

Rosenberg et al., Phosphonylmethoxyalkyl and Phosphonylalkyl Derivatives of Adenine, *Collect. Czech. Chem. Commun.* (1988), 53: 2753–2777.

V.J. Klosa, Über die Unsetzung von Chinazolon–(4)–derivaten mit Alkylenoxiden, *J. Prakt. Chem.* (1966), 4: 34–40.

Mislyuk et al., Kinetics of the Reaction of Piperazine with 1–R–2,3–Epoxypropanes, *J. Org. Chem. USSR (Engl Trans.)* (1986), 22(12): 2247–2252.

B. Cimetiere and J.M. Julia, Optically active oxiranes synthesis of PAF (Platelet Aggregating Factor), *Bull. Soc. Chim. Fr.* (1991), 128: 926–938.

Rattay et al., Influence of α–branched fatty acid chains on the thermotropic behavior of racemic 1–O–hexadecyl–2–acyl–glycero–3–phosphocholines, *Chem. Phys. Lipids* (1995), 75: 81–91.

Bittman et al., Isosteric Phosphonate Analogs of ET–16–OMe. Synthesis and Biological Evaluation of the Enantiomers of 2'–(Trimethylammonio)ethyl 4–(Hexadecyloxy)–3–methoxybutanephosphonate and 2'–(Trimethylammonio)ethyl 4–(Hexadecylthio)–3–methoxybutanephosphonate, *J. Med. Chem.* (1994), 37: 425–430.

W. Rospond and J. Chlebicki, Reactions of 1–Alkylthio–2,3–Epoxypropanes With Ethanolamines, *Polish J. Chem.* (1984), 58: 1237–1242.

T.K. Todsen et al., Some β–Hydroxypropyl Sulfides and their Derivatives, *J. Am. Chem. Soc.* (1950), 72: 4000–4002.

G.V. Hirth and R. Barner, Synthesis of Glyceryletherphosphatides, *Helv. Chim. Acta* (1982), 65: 1059–1084.

A. Hermetter and F. Paultauf, Procedures for Synthesis of Ether Lipids, pp. 391–393 et seq., H.K. Mangold and F. Paultauf, *Ether Lipids*, Academic Press (1983).

F. Paltauf and A. Hermetter, Preparation of Alkyl Ether and Vinyl Ether Substrates for Phospholipases, *Methods Enzymol.* (1991), 197: 134–149.

(List continued on next page.)

*Primary Examiner*—Floyd D. Higel
*Attorney, Agent, or Firm*—DeWitt Ross & Stevens S.C.; Salvatore R. Conte, Esq.

[57] ABSTRACT

Aminoheterocycle-substituted glycerols of Formula I are disclosed:

$$\begin{array}{l} CH_2-A \\ | \\ CH-B \\ | \\ CH_2-C \end{array} \quad I$$

wherein one of A, B or C is —X—R, wherein X is —O— or —S—, and R is a substituted or unsubstituted $C_{12-24}$ alkyl or alkenyl, the substituent being one or more of halo, $C_{1-3}$ alkoxy or cyano, provided that a double bond of the alkenyl does not originate at the carbon atom bound to X; and another of A, B or C is an aminoheterocycle ring substituent —Het—$NH_2$, wherein Het is a 5 to 11-membered monocyclic, bicyclic or bicyclic fused heterocyclic ring moiety with at least 1 to 4 nitrogens atoms contained within the hetero cyclic moiety, one of which nitrogen atoms is bonded to the glycero carbon; and the remaining A, B, or C substituent is —OH. The compounds of Formula I, isomers, salts, pharmaceutical compositions and appliances incorporating the same, and methods of use thereof are also disclosed.

9 Claims, 2 Drawing Sheets

OTHER PUBLICATIONS

A. Hermetter and F. Paltauf, A New Method For the Detritylation of 1,2–Diradyl–3–O–Tritylglycerols, *Chem. Phys. Lipids* (1981), 29: 191.

Morris–Natschke et al., Synthesis of Sulfur Analogues of Alkyl Lysophospholipid and Neoplastic Cell Growth Inhibitory Properties, *J. Med. Chem.* (1986), 29: 2114–2117.

Morris–Natschke et al., Synthesis of Phosphocholine and Quaternary Amine Ether Lipids and Evaluation of in Vitro Antineoplastic Activity, *J. Med. Chem.* (1993), 36: 2018–2025.

Brachwitz et al., Alkyl–glyceryl–ether–Analoga, *J. Prakt. Chem.* (1979), 321: 775–786.

E.O. Oswald et al., the Synthesis of $^{14}$C– and $^{3}$H–Labeled Glycerol Ethers, *Lipids* (1966), 1: 121.

Kalugin et al., Reactions of 2–[(Organylthio)methyl]oxiranes with Acetic Anhydride and Acetyl Chloride, *Bull. Acad. Sci. USSR (Engl. Transl.)* (1991), 40(7): 1391–1394.

AMINOHETEROCYCLE-SUBSTITUTED GLYCEROLS

FIELD OF THE INVENTION

The present invention relates to certain glycerols substituted with an aminoheterocycle moiety on the glyceryl backbone, and to pharmaceutical compositions thereof. These compounds possess growth promoting activity that has utility in enhancing tissue repair and wound healing.

DESCRIPTION OF THE PRIOR ART

All of the references cited below are incorporated herein by reference in their entireties.

Glycerol derivatives containing an aryl heterocycle, such as purine, adenine and the like, have been shown to exhibit antiviral activity. For example, the broad spectrum antiviral activity against several DNA and RNA viruses of (S)-9-(2', 3'-Dihydroxypropyl)adenine and (S)-9-(3'-hydroxy-2'-phosphonyl-methoxypropyl)adenine is reported in DeClercq et al., *Science* (1978) 200: 563–565 and DeClercq et al., *Nature,* (1986) 323: 464–467. Glycerol derivatives in which one hydroxy group is substituted by a heterocycle, such as, adenine, cytosine, uracil, and the like, are reported in the literature, see, for example, Ueda et al., *J Heterocyl. Chem.* (1971) 8: 827–829, Hiller et al., *Nucleic Acids Research* (1976) 3: 721–727, A. Holy, *Collect. Czech. Chem. Commun.* (1978) 43: 3444–3465, and A. Holy, et al., *J Med. Chem.* (1996) 39: 4073–4088.

The preparation of (RS)-9-(2'-hydroxy-3'-octyloxypropyl)adenine is reported by Rosenberg et al., *Collect. Czech. Chem. Commun.* (1988) 53: 2753–2777 (2768); the synthesis of (RS)-3-(2'-hydroxy-3'-dodecyloxypropyl)quinazalin-4-one is disclosed by Klosa, V. J.; *J Prakt. Chem.* (1966) 4: 34–40. Also disclosed is the synthesis of (RS)- 1-(2'-hydroxy-3'-butyloxypropyl) piperazine by Mislyuk et al., *J Org. Chem.* USSR (Engl. Transl.) (1986) 22 (12): 2247–2252. The syntheses of 1-[3'-($R_1$'-oxy)-2-hydroxypropyl]imidazole ($R_1$=$C_1$ to $C_{10}$ alkyl) and 1-[3'($R_1$'-thio)-2'-hydroxypropyl]imidazole ($R_1$=$C_1$ to $C_{10}$ alkyl) is disclosed in U.S. Pat. No. 4,036,974.

Applicants are unaware, however, of the hereinafter described aminoheterocycle substituted glycerols and their utility as growth promoting agents to enhance tissue repair and wound healing.

DESCRIPTION OF THE INVENTION

Figure 1:
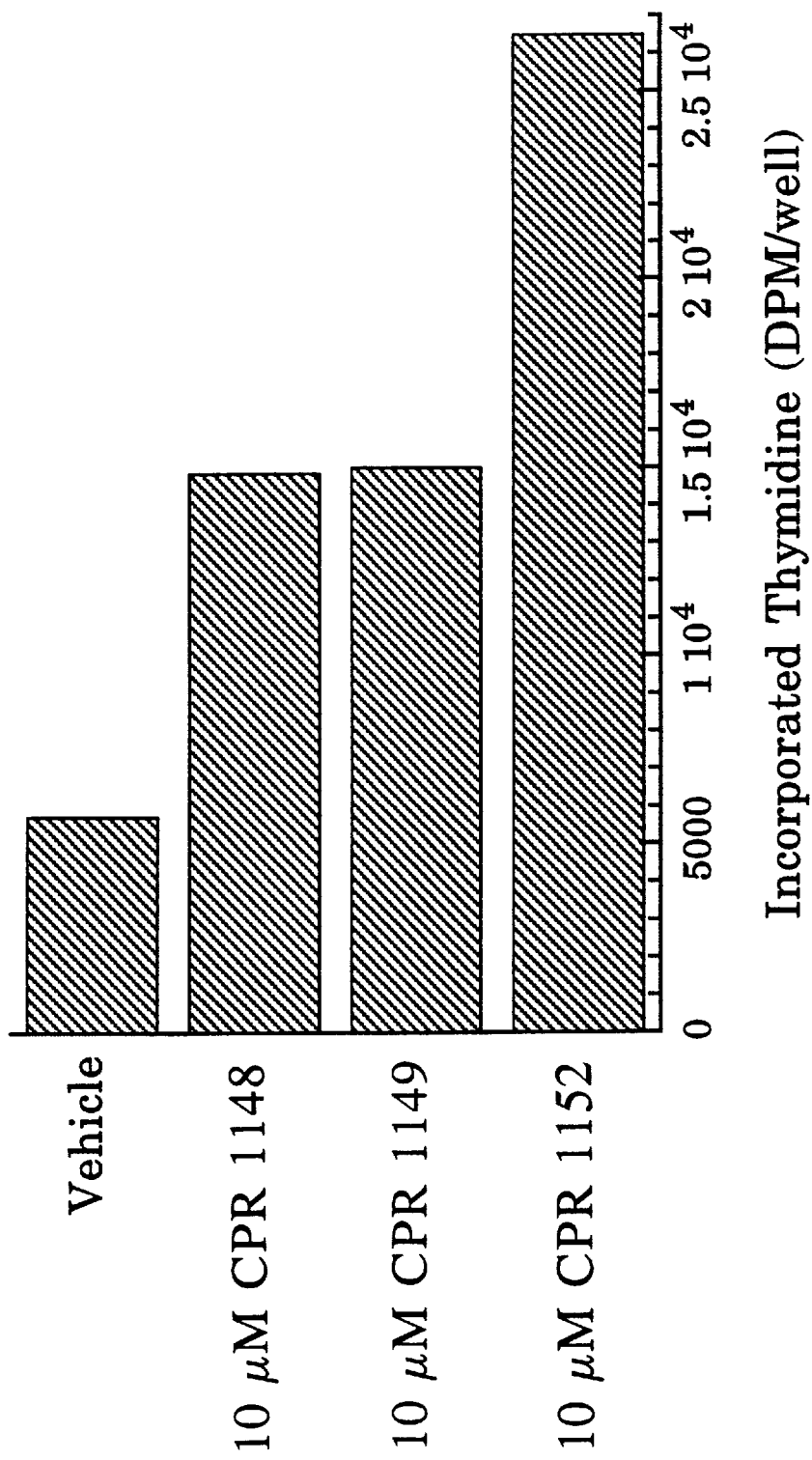
FIG. 1 is a graphical representation of results from an in vitro assay evaluating DNA synthesis in human fibroblast tissue by three compounds of the invention, designated CPR 1148, CPR 1149 and CPR 1152.

The subject invention relates to certain novel glycerols substituted with an amino-heterocycle moiety on the glyceryl backbone, to pharmaceutical compositions thereof and to a method of promoting wound healing and inducing tissue growth by use of said substituted glycerols. The subject substituted glycerols are represented by the general Formula I:

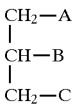

wherein one of A, B or C is the fatty ether substituent —X—R, wherein X is oxygen (—O—) or sulfur (—S—), and R is a substituted or unsubstituted, linear or branched-chain $C_{12\text{-}24}$ alkyl or alkenyl, the substituent being one or more of halo, $C_{1\text{-}3}$ alkoxy or cyano, provided that a double bond of the alkenyl does not originate at the carbon atom bound to X; and another of A, B or C is an aminoheterocycle ring substituent —Het—$NH_2$, wherein Het is a 5 to 1 1-membered monocyclic, bicyclic or bicyclic fused heterocyclic ring moiety with at least 1 to 4 nitrogens atoms contained within the heterocyclic moiety, one of which nitrogen atoms is bonded to the glycero carbon; and the remaining A, B, or C substituent is —Y, wherein —Y is a hydroxyl group (—OH), and further provided that A, B and C are each a different substituent.

More particularly, the subject aminoheterocycle substituted glycerols may be represented by the general Formulas Ia, Ib and Ic (collectively referred to as the Formula I compounds):

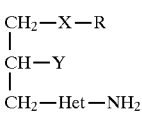

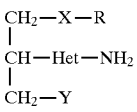

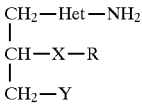

wherein X, R, Het, and Y are as described above.

As used herein, the terms "glycero" or "glyceryl backbone" refer to the three-carbon chain ($CH_2$—CH—$CH_2$) to which the other identified substituents are attached. The term "halo" represents fluoro, bromo, chloro and iodo.

Typical of the heterocyclic ring moieties included within the term "Het" are such 5–11 membered monocyclic and bicyclic fused ring entities as pyrrolyl, pyrazolyl, imidazolyl, 1,2,3-triazolyl, 1,2,4-triazolyl (also denoted as 1-triazolyl), tetrazol-1-yl, indazolyl, benzimidazolyl, benztriazolyl, guaninyl and the like, with purinyl, 2-(1H)-pyrimidinonyl and 2,4-(1H,3H)-pyrimidinedionyl preferred. The Het substituent may also be substituted with one or more substituents, (preferably just one substituent) such as $C_{1\text{-}3}$ alkyl, $C_{1\text{-}3}$ alkoxy or a polar substituent such as fluoro, cyano, nitro or methylsulfono. The Het substituent may also include a heterocyclic ring with an oxygen atom attached to one or more of the ring carbon atoms via a double bond (═O), as in a carbonyl group. Typical of such substituted heterocyclic ring moieties are, for example, 5-fluoro-2,4-(1H,3H)-pyrimidinedionyl and 5-fluoro-2-(1H)-pyrimidinonyl and the like. As used hereinafter, the term "amino-Het-Compound" represents the heterocyclic ring moiety with its additional amino moiety and hydrogen atom, i.e., $H_2N$—Het—H, for example, aminopyrrole, aminopyrazole, aminoimidazole, aminotriazole, adenine, cytosine, uracil, guanine and the like.

It is preferred that the —$NH_2$ group of —Het—$NH_2$ is attached to a carbon atom within the Het ring system.

The compounds of Formula I may exist in isomeric form. For example, the compounds of Formula I have an asymmetric carbon at the C-2 position of the glyceryl moiety, and, consequently, they can exist in the form of different combinations of R- and S- isomeric forms as enantiomers or racemates.

In addition, cis and trans geometric isomers may also be present in the subject compounds, for example, when R in Formula I is $C_{12}$–$C_{24}$ alkenyl, due to the cis or trans configuration inherent with the double bond. Thus, by starting with an appropriate cis or trans precursor, the corresponding end product of Formula I will be obtained.

All racemic and isomeric forms of the compounds of Formula I, including pure enantiomeric, diastereomeric and geometric isomers and mixtures thereof, are within the scope of this invention. Unless otherwise specified, the compounds described in the Examples, below, are in racemic form.

The invention also comprehends salts of the Formula I compounds. Such salts include acid addition salts such as those from inorganic acids such as hydrochloric, nitric, and the like acids, or from organic acids such as citric, lactic and the like organic acids. The salts of the invention are made by conventional methods well known to those skilled in the art. The salts for therapeutic use of the Formula I compounds are pharmaceutically-acceptable salts, as well understood in the art.

It has now been found that the Formula I compounds, including their pharmacologically active isomers and pharmaceutically-acceptable salts, possess growth promoting activity that has utility in enhancing tissue repair and wound healing. Formula I compounds, including their pharmacologically-active isomers and pharmaceutically-acceptable salts also are useful for treatment of all wounds or surgical healing of skin, soft tissues, bone, cornea, nerve tissue, spinal cord, etc.

The most preferred compounds of Formula I are:

CPR 1148, the compound wherein R is octadecyl, X is O, Het—$NH_2$ is 9'-adenyl and Y is OH, namely, rac-9-[2'-hydroxy-3'-octadecyloxypropyl]-adenine;

CPR 1149, the compound wherein R is octadecyl, X is O, Het—$NH_2$ is 2'-cytosyl and Y is OH, namely, rac-1-[2'-hydroxy-3'-octadecyloxypropyl]-cytosine; and CPR 1152, the compound wherein R is octadecyl, X is O, Het—$NH_2$ is 2'-(5-fluorocytosyl) and Y is OH, namely, rac-5-fluoro-1-[2'-hydroxy-3'-octadecyloxypropyl]-cytosine.

These preferred compounds appear as follows:

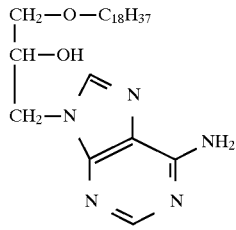

CPR 1148

-continued

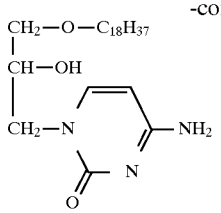

CPR 1149

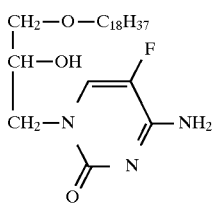

CPR 1152

Other particular compounds of Formula I are:
2-amino-1-[2'-hydroxy-3'-octadecyloxypropyl]-imidazole;
3-amino-1-[2'-hydroxy-3'-octadecyloxypropyl]-pyrazole;
3-amino-1-[2'-hydroxy-3'-octadecyloxypropyl]-triazole;
5-bromo-1-[2'-hydroxy-3'-octadecyloxypropyl]-cytosine;
5-amino-1-[2'-hydroxy-3'-octadecyloxypropyl]-indazole;
2-amino-6-chloro-9-[2'-hydroxy-3'-octadecyloxypropyl]-purine;
9-[2'-hydroxy-3'-octadecyloxypropyl]-guanine;
2-amino-1-[2'-hydroxy-3'-octadecylthiopropyl]-imidazole;
3-amino-1-[2'-hydroxy-3'-octadecylthiopropyl]-pyrazole;
3-amino-1-[2'-hydroxy-3'-octadecylthiopropyl]-triazole;
5-fluoro-1-[2'-hydroxy-3'-octadecylthiopropyl]-cytosine;
5-bromo-1-[2'-hydroxy-3'-octadecylthiopropyl]-cytosine;
5-amino-1-[2'-hydroxy-3 '-octadecylthiopropyl]-indazole;
2-amino-6-chloro-9-[2'-hydroxy-3'-octadecylthiopropyl]-purine;
9-[2'-hydroxy-3 '-octadecylthiopropyl]-guanine;
9-[2'-hydroxy-3 '-(9-cisoctadecenyloxy)propyl]-adenine; and
9-[2'-hydroxy-3'-hexadecyloxypropyl]-adenine.

Chemistry

The compounds of the present invention may be prepared by the stepwise procedures outlined in Reaction Schemes 1–6 and in the subsequent Examples. As used in Reaction Schemes 1–6, the symbols R and Het are as previously defined. The thus-obtained compounds in the Reaction Scheme 1–6 may be purified by conventional methods of the art, e.g. chromatography, recrystallization, etc.

The compounds of Formula I have an asymmetric carbon atom at the C-2 position of the glyceryl backbone in their structure, and consequently they may exist in the form of different R and S isomeric forms (enantiomers) or racemates. Substantially pure forms of the R- and S- isomer may be obtained, substantially free of the other, by the application of art-known resolution methodologies such as, for example, by selective crystallization or column chromatography, or by starting their preparation from the R- or S- isomer of an appropriate precursor, for example, the starting compound (A) depicted in Reaction Scheme I.

In addition, cis and trans geometric isomers may also be present in the subject compounds, e.g. when R is a $C_{12}$–$C_{24}$ alkenyl, due to the cis or trans configuration inherent with the double bond. Thus, by starting with an appropriate cis or trans precursor, the corresponding end product of Formula I will be obtained.

Working-up the individual stepwise products indicated in the Reaction Schemes is advantageously carried out by standard methodologies, for example, by evaporating down the reaction solution or precipitating the product from the reaction solution by dilution with appropriate antisolvents. The crude intermediate products obtained may be quite suitable, without further purification operations, for the preparation of the final products which then may be purified. Particularly suitable methods for purifying the Formula I compounds are the conventional chromatographic methods, such as preparative thin-layer chromatography (TLC), column chromatography, adsorption chromatography, medium pressure liquid chromatography (MPLC), high performance liquid chromatography (HPLC) or kinetic resolution.

REACTION SCHEME 1

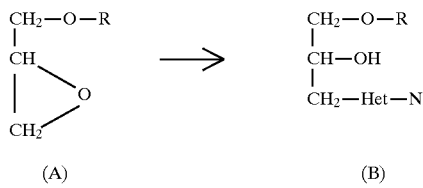

(A)            (B)

The compounds of Formula (A) are commercially available or are known in the literature or are obtainable by art-recognized procedures. See, for example, B. Cimetiere and J. M. Julia, *Bull. Soc. Chim. Fr.* (1991) 128: 926–938, Rattay et al., *Chem. Phys. Lipids* (1995) 75: 81–91, and Bittman et al., *J. Med. Chem.* (1994) 37: 425–430. Conversion of compounds of Formula (A) to compounds of Formula (B) is accomplished by the procedure reported by Ueda et al., *J. Heterocyclic Chem.* (1971) 8: 827–829.

In a typical reaction, a mixture of a compound of Formula (A), in an aprotic solvent such as dimethylformamide, dimethyl sulfoxide, 1,4-dioxane and the like, along with trace amounts of anhydrous potassium carbonate, and slight excess or approximately one equivalent of the heterocyclic amine, for example, adenine, cytosine, fluorocytosine and the like, is stirred at elevated temperatures, preferably 60°–90° C. for 24–48 hours under a nitrogen atmosphere. Conventional work-up of the reaction mixture, for example, with appropriate organic extraction solvents, aqueous washes, drying, or solvent evaporation, followed by conventional chromatographic methods, such as preparative thin-layer chromatography (TLC), column chromatography, adsorption chromatography, medium pressure liquid chromatography (MPLC), high pressure liquid chromatography (HPLC) or kinetic resolution affords the pure product (B).

REACTION SCHEME 2

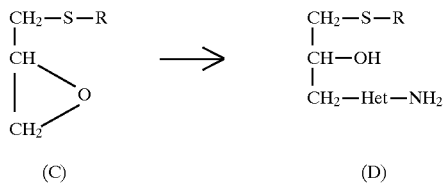

(C)            (D)

The compounds of Formula (C) are known in the literature or are obtainable by art-recognized procedures. See, for example, W. Respond; J. Chlebicki, *Polish Journal of Chemistry* (1984) 58: 1237–1242, T. K Todsen; C. B. Pollard; E. G. Rietz, *J. Am. Chem. Soc.* (1950) 72: 4000–4002. Treatment of compounds (C) with heterocyclic amines, as described in Scheme I, results in compounds of Formula (D). The thus obtained compounds can be purified by conventional methods, as described in Reaction Scheme 1.

REACTION SCHEME 3

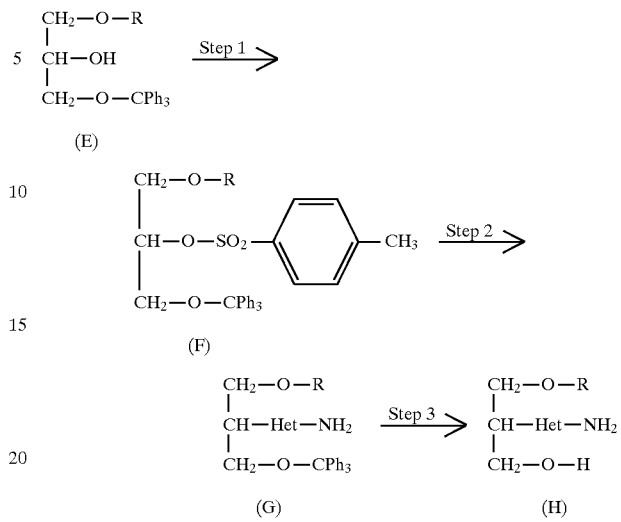

(Ph = $C_6H_5$)

Step 1

The compounds of Formula (E), wherein $P_h$=phenyl, are known in the literature or are obtainable by art-recognized procedures. See, for example, G. V. Hirth, and R. Barner, *Helv. Chimica Acta* (1982) 65: 1059–1084, A. Hermetter and F. Paltauf, *Procedures for the Synthesis of Ether Lipids*, p. 393 et. seq., in H. K. Mangold and F. Paltauf, "Ether Lipids", Academic Press, 1983, and F. Paltauf and A. Hermetter, *Methods in Enzymol.* (1991) 197: 134–149. A solution of Compound (E) in an amphoteric aprotic solvent, e.g. pyridine, tetrahydrofuran, 1,4-dioxane and the like, is added dropwise with stirring to a solution of p-toluenesulfonyl chloride (tosyl chloride) with the same solvent. The reaction mixture may be maintained with stirring at room temperature until the reaction is essentially completed, and then subjected to conventional work-up, for example, with appropriate organic extraction solvents, aqueous washes, drying, solvent evaporation, recrystallization and the like procedures, to yield the desired 2-O-p-toluenesulfonyl derivative of Formula (F).

Step 2

Compound (F) is reacted with a stoichiometric amount of the desired amino-Het—H compound in anhydrous dimethyl sulfoxide in the presence of a base, such as sodium dimethyl-sulfinylmethide, sodium hydride or potassium carbonate. Elevated temperatures are employed to enhance the rate of reaction, e.g. about 100° C. After the reaction is completed, conventional work-up yields the desired 2-Het—$NH_2$ derivative (G).

Step 3

Removal of the triphenylmethyl (trityl) moiety in Compound (G) to yield Compound (H) is readily accomplished by art-recognized procedures, e.g. by reaction with boron trifluoride in an appropriate organic solvent, for example, methanol, at low to ambient temperature, followed by conventional work-up. See, for example, A. Hermetter and F. Paltauf, *Chem. Phys. Lipids* (1981) 29:191.

REACTION SCHEME 4

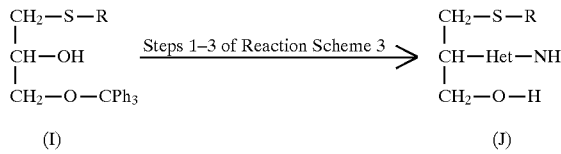

Starting with the thioalkyl compounds of Formula (I), instead of compounds of Formula (E), and following the steps 1, 2 and 3 of Reaction Scheme 3, thioalkyl compounds of Formula (J) are obtained. Compounds of Formula (I) are known in the literature or are obtainable by art-recognized procedures. See, for example, Morris-Natschke et al., *J. Med. Chem.* (1986) 29: 2114–2117 and Morris-Natschke et al., *J. Med. Chem.* (1993) 36: 2018–2025.

REACTION SCHEME 5

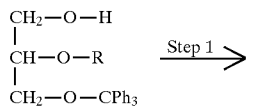

(K)

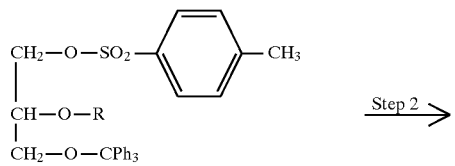

(Ph = $C_6H_5$)

Step 1

The compounds of Formula (K) are known or can be prepared by the procedure of Brachwitz et al., *J. Prakt. Chem.* (1979) 321: 775–786. Tosylation of compounds of Formula (K) is effected by p-toluenesulfonyl chloride in anhydrous pyridine at room temperature as described in Step 1 of Reaction Scheme 3. After the reaction is complete, conventional work-up yields the p-toluenesulfonyl derivatives of Formula (L).

Step 2

Compound (L) is reacted with the desired amino-Het-compound as described in Step 2 of Reaction Scheme 3 to yield the amino-Het-derivative of Formula (M).

Step 3

Removal of the trityl moiety in Compound (M) to yield Compound (N) is readily accomplished by art-recognized procedures, e.g. by reaction with boron trifluoride in an appropriate organic solvent, for example, methanol, at low to ambient temperature, followed by conventional work-up. See A. Hermetter and F. Paltauf, *Chem. Phys. Lipids* (1981) 29:191 as described in step 3 of Reaction Scheme 3.

REACTION SCHEME 6

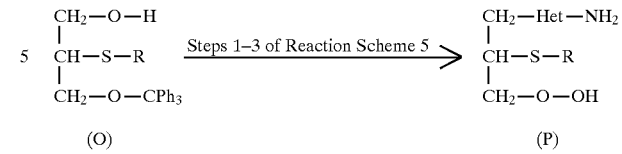

Starting with the compounds of Formula (O), instead of compounds of Formula (K) of Reaction Scheme 5, and following the steps 1, 2 and 3 of Reaction Scheme 5, the corresponding compounds of Formula (P) are obtained. Compounds of Formula (O) are obtainable by tritylation of the corresponding 2-S-alkylglycerol, which can be prepared by similar methodology employed for the corresponding 2-O-alkylglycerol as reported by Oswald et al., *Lipids* (1966) 1: 241–246. Alternatively, compounds of Formula (O) can be obtained by art recognized tritylation of the corresponding 2-S-alkyl-1,3-propanediol. Preparation of 2-S-alkyl-1,3-propanediols can be accomplished by hydrolysis of the corresponding 2-S-alkyl-1,3-diesters which can be prepared as reported in the art. See, for example, Kalugin et al., *Bull. Acad. Sci.* (Engl. Transl.) (1991) 40(7): 1391–1394.

The following Reaction Schemes 7–9 depict the synthetic procedures for preparing compounds of Formula I in which the amino moiety is attached to a nitrogen of the Het moiety.

REACTION SCHEME 7

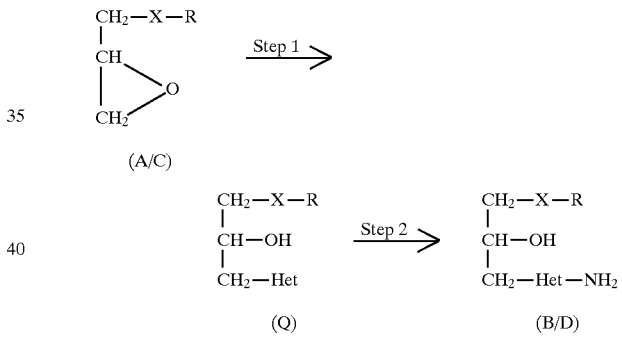

Step 1

The compounds of Formula (A) and Formula (C) wherein X is oxygen or sulfur, respectively, are known in the literature or are obtainable by art recognized procedures, see Reaction Schemes I and 2. Conversion of the appropriate compound of Formula (A) or Formula (C) into compounds of Formula (Q) is accomplished by the procedure reported by Ueda et al., *J. Heterocyl. Chem.* (1971) 8: 827–829.

In a typical reaction, a mixture of a compound of Formula (A)/Formula (C) in an aprotic solvent, such as dimethylformamide, dimethyl sulfoxide, 1,4-dioxane and the like, along with trace amounts of anhydrous potassium carbonate, and a slight excess or approximately one equivalent of the desired heterocycle, for example, piperazine and the like, is stirred at elevated temperatures, preferably 60°–90° C. for 24–48 hours under a nitrogen atmosphere. Conventional work-up of the reaction mixture affords the desired Het compound of Formula (Q).

Step 2

Compounds of Formula (Q) are converted into compounds of Formula (B/D) by methods known in the art, for example, Kirste et al., *Angew. Chem., Int. Ed. Engl.* (1978) 17: 680–681. Compound (Q) is reacted with a stoichiometric amount of hydroxylamine-O-sulfonic acid (HOSA) and sodium or potassium hydroxide in a solvent mixture of tetrahydrofuran-water, a 1:1 mixture of tetrahydrofuran-water mixture most preferred, at 0°–90° C. After the reaction is completed, conventional work-up yields the desired Het-$NH_2$ compound of Formula (B)/Formula (D) in which the exocylic amine moiety is bonded to the Het moiety at a nitrogen atom.

REACTION SCHEME 8

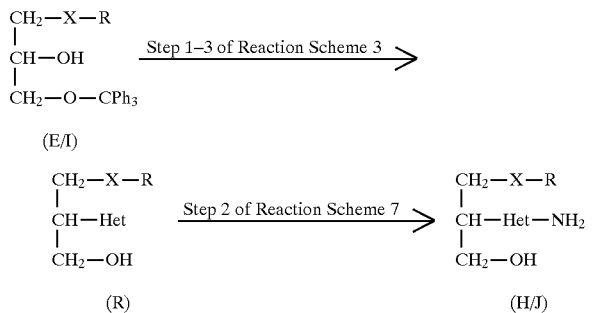

Starting with the compounds of Formula (E) or Formula (I) wherein X is oxygen or sulfur, respectively, and following steps 1, 2 and 3 of Reaction Scheme 3, Het compounds of Formula (R) are obtained. Compounds of Formula (R) are then converted to Het—$NH_2$ compounds of Formula (H) or (J), in which the exocyclic amine moiety is bonded to the Het moiety at a nitrogen atom, by the method described in Step 2 of Reaction Scheme 7.

REACTION SCHEME 9

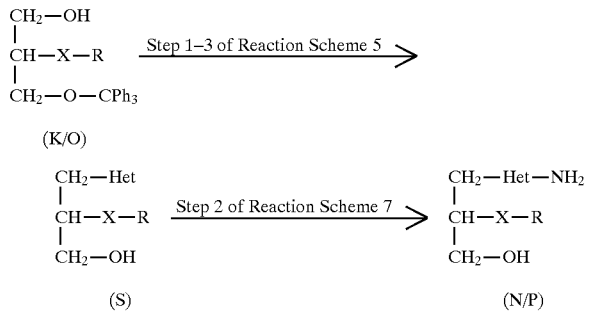

Starting with the compounds of Formula (K) or Formula (O) wherein X is oxygen or sulfur, respectively, and following steps 1, 2 and 3 of Reaction Scheme 5, Het compounds of Formula (S) are obtained. Compounds of Formula (S) are then converted to Het—NH2 Compounds of Formula (N)/Formula (P), in which the exocyclic amine moiety is bonded to the Het moiety at a nitrogen atom, by the method described in Step 2 of Reaction Scheme 7.

Utility

Wounds are internal or external bodily injuries or lesions caused by physical means, such as mechanical, chemical, viral, bacterial or thermal means, which disrupt the normal continuity of structures. Such bodily injuries include contusions, trauma or wounds in which the skin is unbroken, incisions and wounds in which the skin is broken, and the like. Wounds may be caused by accidents, by surgical procedures or by intentional inflictions.

Wound healing consists of a series of processes whereby injured tissue is repaired, specialized tissue is regenerated, and new tissue is reorganized. Wound healing proceeds in three major phases: an inflammation phase (0–3 days), a cellular proliferation phase (3–12 days) and a remodeling phase (3 days–6 months). Cellular proliferation results in granulation tissue formation leading to tissue repair.

When cells are injured or killed as a result of a wound, a wound-healing step is desirable to resuscitate the injured cells and produce new cells to replace the dead cells. An aspect of the subject invention pertains to therapeutic wound-healing compositions utilizing one or more compounds of Formula I, or pharmaceutically-acceptable isomers or salts thereof, as the active wound-healing ingredient. Such compositions are applicable for preventing and reducing injury to mammalian cells and increasing the resuscitation rate of injured mammalian cells. The wound-healing compositions may be used alone or in combination with other wound-healing agents and/or medicaments, for example, an antioxidant, or a mixture of saturated and unsaturated fatty acids wherein the fatty acids are those fatty acids utilized for the repair of cellular membranes and resuscitation of mammalian cells, for example, mono-, di- or triglycerides, or free fatty acids, or mixtures thereof. Aiding cellular proliferation promotes cellular repair.

In general, the types of wounds which may be healed by using the subject therapeutic compositions, comprising a wound-healing compound of Formula I, are those which result from an injury which causes epidermal damage such as incisions (wounds in which the skin is cleanly incised by a sharp edge, as by a cutting instrument) and lacerations (wounds in which the skin is broken by a dull or blunt means, such as traumatic impact). The therapeutic compositions of this invention may also be used to treat various dermatological disorders such as hyperkeratosis, burns, cutaneous ulcers, psoriasis and the like. The subject compositions may also be used orally in the form of a mouth wash or spray to protect and accelerate the healing of injured oral tissue such as mouth sores. The subject compositions may in addition be used in anorectal creams and suppositories to treat such conditions as, for example, pruritus, proctitus, anal fissures and hemorrhoids.

The subject compositions may be used in the form of topical (non-oral and oral) products and ingestible therapeutic products for systemic administration. The ultimate therapeutic wound-healing compositions are readily prepared using methods generally known in the pharmaceutical arts by those having ordinary skill in the art.

Non-oral topical compositions employ non-oral topical vehicles, such as creams, gels, foams, ointments, sprays and the like which are intended to be applied to the skin or body cavity and are not intended to be taken by mouth. Oral topical compositions employ oral vehicles, such as mouthwashes, rinses, oral sprays, dental creams and gels, and the like, which are intended to be taken by mouth but are not intended to be ingested. Ingestible compositions for systemic administration employ ingestible or partly ingestible formulations suitable for making unit dosages in solid form, such as tablets, capsules, chewing confectioneries and the like, and in liquid form, such as solutions, suspensions, syrups and the like.

Methods for healing a wound comprise administering, either systemically and/or topically, the compositions of the present invention to increase the healing rate of the wound. In topical applications, the composition is maintained in contact with the wound for a period of time sufficient to increase the proliferation and resuscitation rate of the cells, for example, until clotting has occurred.

The invention thus provides a method of treating wounds in a mammal afflicted with damaged tissue cells which comprises administering to said mammal an effective wound-healing amount of a Formula I compound, including a pharmaceutically-acceptable isomer or salt thereof.

The wound-healing and cell growth stimulant activity of the herein-described compounds of Formula I and pharmaceutically-acceptable salts thereof may be assayed by many conventional methodologies in the art. Fibroblasts play a major role in tissue repair and wound healing. Enhanced fibroblast growth translates into enhanced wound healing. As demonstrated in the following assays, the subject compounds stimulate fibroblast proliferation and granulation tissue formation, and, accordingly, enhance the healing of wounds in an organized and timely fashion.

Assay A: Stimulation of Fibroblast Growth

Growth stimulatory activity of potential growth factors is evaluated using cultured murine fibroblasts. These cells were serum-starved before treating with test compounds. To estimate relative cell growth, DNA synthesis is measured.

1. Cell line: 3T3 (ATCC CCL-92, attachment dependent).
2. Culture medium: Dulbecco's modified Eagle's medium (DMEM), 90%; fetal bovine serum, 10%; 10 units/ml penicillin; 10 mg/mL streptomycin.
3. Standard culture protocol: in T-150 flasks; 37° C.; 95% air, 5% $CO_2$; 100% humidity:
   a. Culture medium is renewed every three days.
   b. Cell line is passaged when approximately 50% confluent using 0.05% trypsin and 0.53 mM ethylenediaminetetraacetic acid (EDTA) in Hank's balanced salt solution (HBSS) at a 1:10 dilution ratio.
   c. All procedures are performed aseptically in a class II biological safety cabinet using standard BL-2 containment procedures. In order to prevent genetic drift in the cell line, fresh cultures are prepared at approximately monthly intervals with cells thawed from liquid nitrogen storage.
4. Methodology:
   a. After cell passage, determine cell concentration using a hemacytometer;
   b. Adjust cell concentration to 10,000 cells per mL;
   c. Place one mL of the cell suspension in each well of 24-well plates;
   d. Culture plates for 8 hours;
   e. Aspirate culture medium;
   f. Wash each well once with warm (37° C.) DMEM by adding one mL and aspirating;
   g. Add one mL of warm (37° C.) DMEM containing 10 units/mL penicillin and 10 mg/mL streptomycin;
   h. Culture plates for 48 hours;
   i. Dissolve test compounds in dimethyl sulfoxide (DMSO) at 2 mM;
   j. Add 5 mL of vehicle (DMSO) or solutions of test compounds to each well;
   k. Culture plates for 15 hours;
   l. Add 10 mL of DMEM containing 3 mCi [$^3$H] thymidine (70–90 Ci/mmol, DuPont NEN) to each well; The curie, Ci, is the fundamental unit of radioactivity; it is defined as the quantity of nuclide in which $3.7 \times 10^{10}$ disintegrations occur per second.
   m. Culture plates for 5 hours;
   n. Aspirate culture medium;
   0. Add one mL of 10% trichloroacetic acid (TCA) in water to each well;
   p. Refrigerate plates for one hour;
   q. Aspirate liquid and wash each well three times with 10% TCA by adding one mL and aspirating;
   r. Wash each well twice with ethanol by adding one mL and aspirating;
   s. Air dry plates for 20 minutes;
   t. Add 0.5 mL of 0.5M NaOH and 0.1% triton X-100 in water to each well;
   u. Place plates on an orbital shaker for two hours;
   v. Add 0.25 mL of 1M aqueous HCl to each well;
   w. Transfer 0.5 mL of the contents of each well to a scintillation vial;
   x. Add 4 mL of scintillation cocktail to each vial;
   y. Measure the radioactivity associated with each vial in a scintillation counter.
5. Results, which are presented in FIG. 1, indicate that the Formula I compounds, as represented by CPR 1148, CPR 1149, and CPR 1152, induce DNA synthesis in murine fibroblasts.

Assay B: Evaluation of Wound-Healing Potential

1. Preparation of CPR 1152

5mg of CPR 1152 is added to 100 mL of saline in a vial. The vial is warmed to 56° C. in heated tap water, and then sonicated for two minutes at room temperature.

2. Preparation of Impregnated "GELFOAM"® Gelatin Patches

Inject 100 mL of CPR 1152 into each "GELFOAM"® gelatin patch (1 cm$^3$) with a 23 gauge needle and allow to dry at room temperature overnight. Saline (100 mL) is injected into separate "GELFOAM"® gelatin patches with a 23 G needle and dried at room temperature overnight.

3. Guinea Pigs

Female Guinea Pig #1 weight: 1008 g

Female Guinea Pig #2 weight: 900 g

4. Day 1

For each animal, a 2 cm incision was made on the dorsal surface at the posterior border of the scapula. A subcutaneous tunnel was made with a forceps to the posterior lumbar vertebrae. Four "GELFOAM"® gelatin cubes, three containing CPR 1152 and one containing saline, were placed in the tunnel formed within Guinea Pig #1; four "GELFOAM"® gelatin cubes containing saline were placed in the tunnel formed within Guinea Pig #2. The "GELFOAM"® gelatin cubes were disposed about 2.5 cm apart from each other. Incisions were closed with sutures. Animals were given 200 mg/L of tetracycline in their drinking water.

5. Day 2 to Day 6

To prevent infection, 200 mg/L of tetracycline were placed in the drinking water every day; animals were given standard Guinea pig food. No sign of infection nor any abnormal activity was observed.

6. Day 7

Guinea Pig #1 weight: 926 g

Guinea Pig #2 weight: 720 g

The animals were killed by $CO_2$ exposure. All four of the "GELFOAM"® cubes were removed from animal #1 and two "GELFOAM"® cubes were removed from animal #2.

| "GELFOAM" ® Sample No. | Weight (g) |
| --- | --- |
| 1. G. Pig #1 | 0.5729 |
| 2. G. Pig #1 | 0.8579* |
| 3. G. Pig #1 | 0.3469 |
| 4. G. Pig #1 | 0.0717 |
| 5. G. Pig #2 | 0.0882 |
| 6. G. Pig #2 | 0.0938 |

(* "GELFOAM"® cubes 1 and 2 appeared to be within one granulation tissue mass)

Samples 1, 2, and 3 were treated with CPR 1152; samples 4, 5 and 6 were treated with saline.

The cubes containing the CPR 1152 were surrounded by granulation tissue. The cubes containing the saline as controls had no reactive tissue growth other than what appeared to be a fibrous covering.

Figure 2:
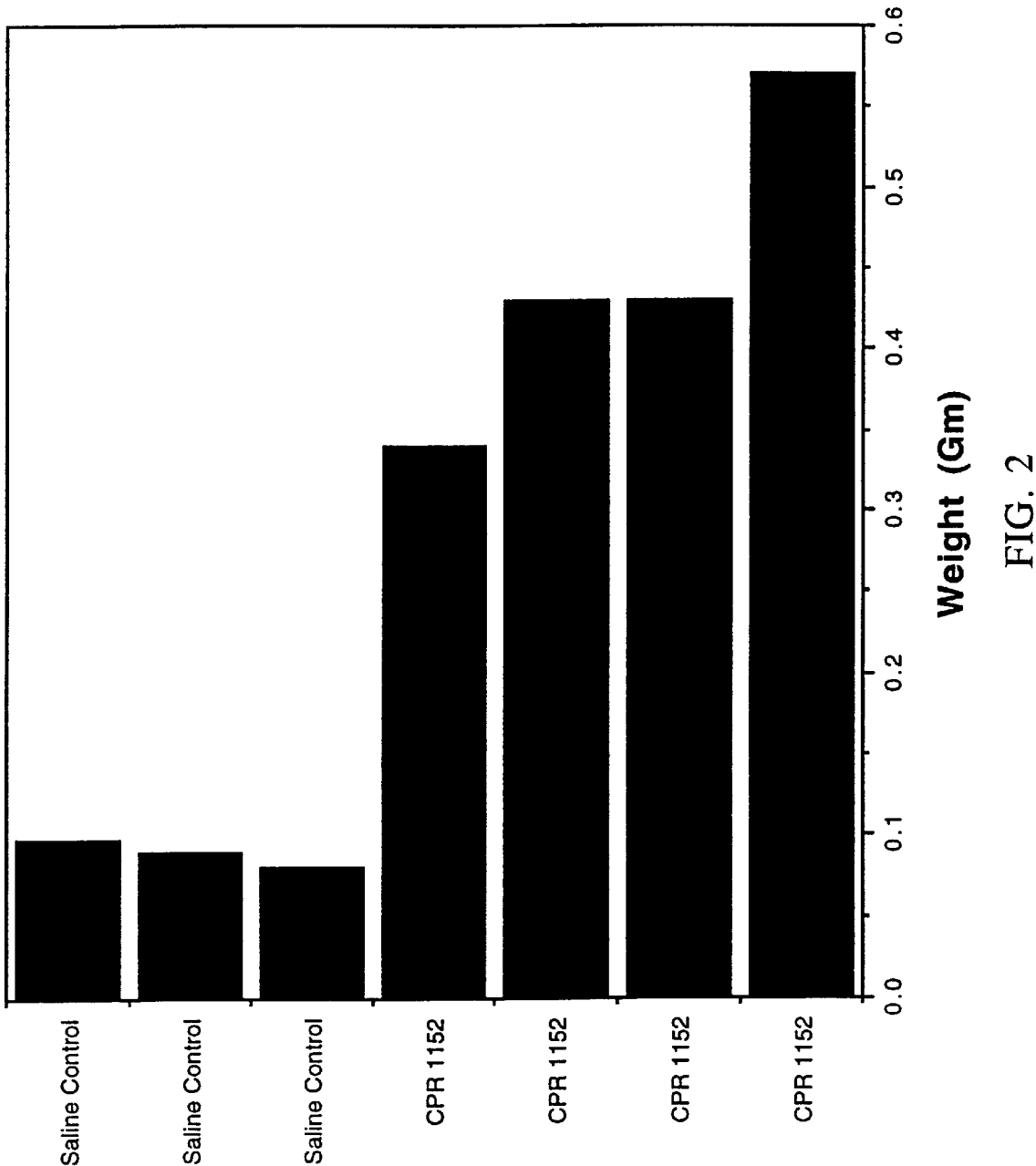
FIG. 2 is graphical representation of results from an in vivo assay evaluating wound-healing potential in Guinea Pigs by one of the compounds of the invention, designated CPR 1152.

7. Results, which are presented in FIG. 2, indicate that CPR 1152 enhances granulation tissue formation.

Pharmaceutical Compositions

Another aspect of the invention provides pharmaceutical compositions for medical use, comprising an active compound, i.e., a Formula I compound or a pharmaceutically-acceptable salt thereof, together with an acceptable carrier therefor and optionally other therapeutically active ingredients. The carrier must be pharmaceutically acceptable in the sense of being compatible with the other ingredients of the formulation and not deleterious to the recipient thereof. The compositions include compositions suitable for oral, topical, or parenteral (including subcutaneous, intramuscular and intravenous) administration or for application by a suitable wound-healing material that contains the Formula I compound. Formula I compounds, including their pharmacologically active isomers and pharmaceutically-acceptable salts, also are useful for treatment of all wounds or surgical healing, such as skin, soft tissue, bone, cornea, nerve tissue, and spinal cord wounds and the like.

The formulations may conveniently be presented in unit dosage form and may be prepared by any of the methods well known in the art of pharmacy. The term "unit dosage" or "unit dose" is denoted to mean a predetermined amount of the active ingredient sufficient to be effective for treating each of the indicated activities. All methods include the step of bringing the active compound into association with a pharmaceutically-acceptable carrier and one or more optional accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, creams, gels, ointments, cachets, tablets, each containing a predetermined amount of the active compound; as a powder or granules; or in liquid form, e.g., as suspension, solution, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulations suitable for parenteral administration conveniently comprise a sterile preparation of the active compound in, for example, a polyethylene glycol solution which is preferably isotonic with the blood of the recipient. Useful formulations also comprise concentrated solutions or solids containing the compound of Formula I which upon dilution with an appropriate solvent give a solution suitable for parenteral administration.

Preparations for topical applications comprise creams, lotions, gels, ointments, aerosol sprays, etc., and pharmaceutically-acceptable vehicles therefore, such as lower aliphatic alcohols, polyglycerols such as glycerol, polyethylene glycerol, ester of fatty acids, oils and fats, silicones, and other conventional topical carriers. In such topical formulations, the compounds of Formula I are preferably utilized at concentration of from about 0.1% to 5.0% by weight.

Preparations for local surgical applications for treating a wound comprise sterile dressings suitable for wound care in which the compounds of Formula I are preferably utilized at concentrations effective for the intended site, in general, from about 0.1 to 100 mg per $cm^2$ of wound contacting surface.

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of compound of Formula I required to be effective for the indicated activities will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. In general, a suitable effective dose for systemic administration is in the range of about 0.5 to about 500 mg/kg body weight per day, preferably in the range of about 5 to about 350 mg/kg per day, calculated as the non-salt form of Formula I. The total daily dose may be given as a single dose, multiple doses, e.g., two to six times per day, or by intravenous infusion for a selected duration. If discrete multiple doses are indicated, treatment might typically be 200 mg of a compound of Formula I given 3 to 4 times per day. Dosages above or below the range cited above are within the scope of the present invention and may be administered to the individual patient if desired or necessary. In general, the pharmaceutical compositions of this invention may contain from about 0.5 to about 500 mg per unit dosage form.

Pharmaceutical Appliances

In still another aspect of this invention, the therapeutic wound-healing composition is incorporated into a pharmaceutical appliance which may be in the form of a substrate such as a suture, gauze, surgical sponge, bandage, adhesive strip patch, and the like. The amounts of the subject composition so employed are readily determined by those skilled in the art without the need for undue experimentation. The exact amount of the particular composition employed is subject to such factors as the type and concentration of the composition and the type of hemostatic appliance employed. Thus, the effective amount of therapeutic wound-healing composition may be varied in order to obtain the result desired in the final product and such variations are within the capabilities of those skilled in the art without the need for undue experimentation.

The pharmaceutical appliances of the invention are suitable for use with mammals, both human and animal. Thus, companion, livestock, and wild animals can be treated with such appliances, in addition to humans.

In a particular embodiment, the therapeutic wound-healing composition may contain from about 0.1% to about 10% by weight of the active Formula I compound as the active ingredient. A variety of traditional ingredients may optionally be included in the composition in effective amounts, such as buffers, preservatives, antioxidants and the like. In terms of ion additives, calcium chloride is generally a preferred additive for introducing a calcium ion into the pharmaceutical appliance. The therapeutic wound-healing composition may be in a solvent and may be incorporated into the pharmaceutical appliance, for example, by dipping, or may be absorbed onto the surface of the pharmaceutical appliance, for example, by coating or spraying or applying a cream-like composition thereon. Advantageously, the wound contacting surface may contain from about 0.2 to about 200 mg per $cm^2$ of the active ingredient.

An exemplified embodiment of a particular pharmaceutical appliance of a wound covering comprises a shaped, preferably flexible, material suitable for medical application to a wound, such as, for example, cotton, gelatin foam, collagen, cellulose, alginate, hydrogels and the like, which is impregnated, or which contains on its wound-treating surface, an effective wound-healing or blood-stanching amount of one or more Formula I compounds. The particular material must be such as to allow delivery of the active wound-healing composition to the wound surface. Drying and sterilization of the pharmaceutical appliance, which is desirable, may be readily accomplished by art-recognized methods, for example, by lyophilization and radiation, respectively. The pharmaceutical appliances may be manufactured in any convenient form, for example, spherically, conically, cuboidally, cylindrically or as small squares or rectangles, such as for packing into a body cavity. Such an embodiment is useful, for example for a dental cavity resulting from tooth extraction. Additionally, the appliance can be configured into a tampon, for example, for epistaxis (profusely bleeding nostril) or other void. Obviously, a prefabricated appliance in sheet form may be cut to size according to its intended use.

The dimensions of the shaped material may vary depending upon the particular wound application. For example, a particular wound dressing may vary in thickness from about 1 to about 10 mm and a width and length from about 1 to about 20 cm, although obviously other dimensions may be utilized as warranted. The dressing may also have adhesive substances attached to its periphery, for example, an adhesive strip or an adhesive bandage, to permit adhesion of the dressing to the skin surrounding the wound so that constant contact of the active ingredient impregnated material is maintained at the wound surface. It may be important that the dressing material is moisture-vapor permeable so that it allows excessive moisture to evaporate from the wound, and it may be air permeable.

For example, embodiments may be made by applying to the wound-contacting surface a pharmaceutical appliance made from, for example, a gauze pad, a gelatin foam, a collagen matrix and the like appliances, which contains an effective wound-healing amount of the Formula I compound when applied to the wound site. The compound may first be dissolved in an appropriate pharmaceutically-acceptable solvent, for example, a phosphate-buffered saline or a weak acidic solution, and then applied to the appliance material, for example, by dipping, spraying, coating, etc., to provide a final wound-healing effective amount, for example, from about 0.2 to about 200 mg per $cm^2$, deliverable to the surface of the wound.

An embodiment particularly useful for small cuts and wounds to the skin, is the commercially available adhesive strip or adhesive bandage, for example, those commercially available from Johnson & Johnson of New Brunswick, N.J. under the brand name "BAND-AID", the wound contacting pad of which has been applied with an appropriate composition containing the hemostatic agent of Formula I.

Another particular embodiment is a hemostatic patch, which rapidly stanches the flow of blood from a lesion on a parenchymal organ, for example, such as the liver, kidney, spleen, pancreas or lungs, by pressing it against the surface of the organ for a period of time sufficient for clotting to occur at the interface between the hemostatic patch and the lesion and for bleeding to be substantially arrested. The particular patch may be produced by applying an appropriate composition containing a Formula I compound to a fairly rigid sheet of biodegradable foam, such as an absorbable gelatin material, and compressing the dry sheet to produce a flexible sheet which conforms to the contours of the organ without the need of pre-moistening. The patch is held in place against the biological surface preferable with light pressure, preferably by means of a sterile saline soaked sponge, by means of sterile gauze, by a sterile elastic bandage, or other appropriate dry sterile material.

The wound-contacting surface of a particular pharmaceutical appliance of this invention may be coated with a color indicator to assist the user, such as yellow vitamin $B_2$ (riboflavin) or a suitable dye such as hemin. By color coding the appliance, the user knowingly avoids touching or otherwise contaminating the wound-contacting surface of the appliance.

Drying the treated pharmaceutical appliance is accomplished by conventional methods, for example, by lyophilization or by treating with heat. Other drying procedures appropriate for the particular appliance may also be employed so long as the drying procedure does not limit the delivery of the active compound to the wound site or result in compound decomposition. Alternatively, the appliance may be dried by simply maintaining it at room temperature for a suitable period.

The subject invention thus provides an article of manufacture, namely, a pharmaceutical appliance which comprises a therapeutically acceptable material (or matrix), preferably flexible, suitable for medical application to a mammalian wound surface and an effective wound-healing amount of a Formula I compound incorporated in or on said material at the wound-contacting surface thereof. Such appliances provide contact of the Formula I compound at the wound site to prevent and reduce injury to mammalian cells, to increase the resuscitation rate of injured mammalian cells, and to stanch bleeding at the wounded surface.

The subject invention also provides a method for inhibiting or stanching bleeding from a wound which comprises applying to the wounded surface a herein described pharmaceutical appliance. A particular application comprises pressing (manually or otherwise) said pharmaceutical appliance against the wounded surface for a period of time until clotting has occurred at the interface between the pharmaceutical appliance and the wounded surface.

In a preferred embodiment, the pharmaceutical appliance provides an effective hemostatic amount of a compound selected from the group consisting of:

9-[2'-hydroxy-3'-octadecyloxypropyl]-adenine,
1-[2'-hydroxy-3'-octadecyloxypropyl]-cytosine, and
5-fluoro-1-[2'-hydroxy-3 '-octadecyloxypropyl]-cytosine,
when applied to the wounded surface.

Prior to applying the particular pharmaceutical appliance, it is recommended to soak the appliance in sterile saline solution. Such a step is not required, however. Use of the appliance according to the invention, without first soaking in saline solution, permits quick and simple application of the appliance in field situations, such as may be encountered by an emergency medical technician or a military health-care worker.

A particular use of the pharmaceutical appliances according to the present invention is to inhibit or completely stop bleeding of a parenchymal organ. An additional use for such appliance includes curbing bleeding of tissues during surgery such as, but not limited to, internal/abdominal, vascular (particularly for anastomosis), urological, gynecological (particularly for an episiotomy), thyroidal, neurological, ENT, tissue transplant uses, and dental surgeries.

Another use of the subject pharmaceutical appliances includes topical treatment, such as for burns or tissue transplants, and which may include additives such as anti-infective medicaments. Bactericides, fungicides and other wound-healing agents, for example, neomycin, bacitracin, epsilon aminocaproic acid (EACA) and the like.

One or more layers of wound dressing material, preferably a layer which aids in absorption of blood or other exudants, can be applied to the particular pharmaceutical appliance. Such an additional layer(s) can be made as an integral part of the appliance, thereby creating a thicker appliance. Alternatively, the layer(s) may be applied as a supplement to the backside (non-wound-contracting surface) of the appliance. Particularly for topical use, the layer(s) can contain superabsorbents to wick exudant solution from the wound site. It is advised that for the appliances intended for internal surgical applications, where an added layer(s) is integral with the patch, the layer(s) should be both biodegradable and pharmaceutically acceptable.

The following examples are intended to illustrate and not to limit the scope of the present invention. Examples 1–4 are illustrative of Reaction Scheme 1. Examples 5–7 are illustrative of Reaction Scheme 2. Examples 8–12 are illustrative of Reaction Scheme 3. Example 13 is illustrative of Reaction Scheme 4. Examples 14–17 are illustrative of Reaction Scheme 5. Example 18 is illustrative of Reaction Scheme 6.

EXAMPLE 1

9-[2'-Hydroxy-3'-octadecyloxypropyl]-adenine (CPR 1148)

A mixture of adenine (0.829 g, 6.10 mmol), anhydrous potassium carbonate (45 mg) and rac-1,2-epoxy-3-octadecyloxypropane (2.0 g, 6.13 mmol) in anhydrous dimethylformamide (10 mL) is stirred at 70°–75° C. for 20 hours under a nitrogen atmosphere. The reaction mixture is filtered directly without cooling, and the filtrate is concentrated in vacuo to afford a white residue. The residue is stirred with 95:5 (v/v) chloroform-methanol. The insoluble solid is filtered, purified by chromatography, and dried in vacuo to give 0.9 g (31.8%) of 9-[2'-hydroxy-3'-octadecyloxypropyl]-adenine (CPR 1148): Thin-layer Chromatography (TLC); 4×8 cm silica gel 60, 0.25 mm thickness, 10:2:0.2 (v/v/v) $CHCl_3$-$CH_3OH$-30% aqueous ammonia ($R_f$ value=0.65); mp 151°–152° C.

EXAMPLE 2

1-[2'-Hydroxy-3'-octadecyloxypropyl]-cytosine (CPR 1149)

rac-1,2-Epoxy-3-octadecyloxypropane (2.0 g, 6.13 mmol) is added to a mixture of cytosine (1.0 g, 9.0 mmol) and anhydrous potassium carbonate (40 mg) in dimethyl formamide (25 mL) over a 30 minute period under a nitrogen atmosphere. The resultant mixture is stirred at 80°–90° C. (oil bath temperature) for 48 hours. The reaction mixture is cooled to room temperature and concentrated in vacuo to leave a residue. The residue is stirred with chloroform (50 mL). The undissolved material is filtered in vacuo, and the filtrate is concentrated in vacuo, purified by chromatography and dried in vacuo to afford 1.0 g (37%) of 1-[2'-hydroxy-3'-octadecyloxypropyl]-cytosine (CPR 1149): Thin-layer Chromatography (TLC; 4×8 cm silica gel 60, 0.25 mm thickness): 10:2:0.2 (v/v/v) $CHCl_3$-$CH_3OH$-30% aqueous ammonia ($R_f$ value=0.66); mp 153°–154° C.

EXAMPLE 3

5-Fluoro-1-[2'-hydroxy-3'-octadecyloxypropyl]-cytosine (CPR 1152)

A mixture of 5-fluorocytosine (0.80 g, 6.20 mmol), anhydrous potassium carbonate (40 mg) and anhydrous dimethyl formamide (15 mL) is heated to 70° C. under a nitrogen atmosphere. Then rac-1,2-epoxy-3-octadecyloxypropane (2.0 g, 6.13 mmol) is added to this mixture with stirring over a period of 1 hour. The resultant reaction mixture is stirred at 80°–90° C. (oil bath temperature) for 48 hours. The reaction mixture is cooled to room temperature and concentrated under reduced pressure (0.5 mm Hg) to afford the crude product as a cream solid. This crude material is purified by chromatography and dried in vacuo to give 0.6 g (22%) 5-fluoro-1-[2'-hydroxy-3'-octadecyloxypropyl]-cytosine (CPR 1152): Thin-layer Chromatography (TLC; 4×8 cm silica gel 60, 0.25 mm thickness): 8:2 (v/v) $CHCl_3$-$CH_3OH$ ($R_f$ value=0.75); mp 118°–119° C.

EXAMPLE 4

The procedure of Example 3 is followed, except that an equivalent amount of the appropriate heterocyclic amine is utilized in Reaction Scheme 1 to afford the following respective Formula (B) compounds:
9-[2'-hydroxy-3'-hexadecyloxypropyl]-adenine,
2-amino-1-[2'-hydroxy-3'-octadecyloxypropyl]-imidazole,
3-amino-1-[2'-hydroxy-3'-octadecyloxypropyl]-pyrazole,
3-amino-1-[2'-hydroxy-3'-octadecyloxypropyl]-triazole,
5-bromo-1-[2'-hydroxy-3'-octadecyloxypropyl]-cytosine,
5-amino-1-[2'-hydroxy-3'-octadecyloxypropyl]-indazole,
2-amino-6-chloro-9-[2'-hydroxy-3'-octadecyloxypropyl]-purine,
9-[2'-hydroxy-3'-octadecyloxypropyl]-guanine, and
9-[2'-hydroxy-3'-(9-cis-octadecenyloxy)propyl]-adenine.

EXAMPLE 5

9-[2'-Hydroxy-3'-octadecylthiopropyl]-adenine

The procedure of Example 1 is followed except that an equivalent amount of rac-1-alkylthio-2,3-epoxypropane is employed as the starting material in place of rac-1,2-epoxy-3-O-alkyl-propane to yield the title indicated compound of Formula (B).

A mixture of adenine (0.829 g, 6.10 mmol), anhydrous potassium carbonate (45 mg) and rac-1,2-epoxy-3-octadecylthiopropane (2.0 g, 5.83 mmol) in anhydrous dimethyl formamide (10 mL) is stirred at 70°–75° C. for 20 hours under a nitrogen atmosphere. The reaction mixture is filtered directly without cooling and the filtrate is concentrated under reduced pressure to afford a white residue. The residue is stirred with 95:5 (v/v) chloroform-methanol. The insoluble solid is filtered, purified by chromatography, and dried in vacuo to 9-[2'-hydroxy-3'-octadecylthiopropyl]-adenine.

EXAMPLE 6

1-[2'-Hydroxy-3'-octadecylthiopropyl]-cytosine rac-1,2-Epoxy-3-octadecylthiopropane (2.0 g, 5.83 mmol) is added to a mixture of cytosine (1.0 g, 9.0 mmol)

and anhydrous potassium carbonate (40 mg) in dimethyl formamide (25 mL) over a 30 minute period under a nitrogen atmosphere. The resultant mixture is stirred at 80°–90° C. (oil bath temperature) for 48 hours. The reaction mixture is cooled to room temperature and concentrated in vacuo to leave a residue. The residue is stirred with chloroform (50 mL). The undissolved material is filtered in vacuo, and the filtrate concentrated in vacuo, purified by chromatography and dried in vacuo to afford 1-[2'-hydroxy-3'-octadecylthiopropyl]-cytosine.

EXAMPLE 7

By following the procedure for Example 6, except that an equivalent amount of the appropriate heterocyclic amine is utilized with the appropriate 1,2-epoxy-3-alkylthiopropane to yield the following respective Formula (D) compounds:
9-[2'-hydroxy-3'-hexadecylthiopropyl]-adenine,
2-amino-1-[2'-hydroxy-3'-octadecylthiopropyl]-imidazole,
3-amino-1-[2'-hydroxy-3'-octadecylthiopropyl]-pyrazole,
3-amino-1-[2'-hydroxy-3'-octadecylthiopropyl]-triazole,
5-fluoro-1-[2'-hydroxy-3'-octadecylthiopropyl]-cytosine
5-bromo-1-[2'-hydroxy-3'-octadecylthiopropyl]-cytosine,
5-amino-1-[2'-hydroxy-3'-octadecylthiopropyl]-indazole,
2-amino-6-chloro-9-[2'-hydroxy-3'-octadecylthiopropyl]-purine,
9-[2'-hydroxy-3 '-octadecylthiopropyl]-guanine, and
9-[2'-hydroxy-3 '-(9-cis-octadecenylthio)propyl]-adenine.

EXAMPLE 8

1-O-Octadecyl-2-O-p-toluenesulfonyl-3-O-tritylglycerol

A solution of 1-O-octadecyl-3-O-tritylglycerol (173.51 g, 295.63 mmol) in 895 mL water free pyridine is added to a solution of p-toluenesulfonyl chloride (88.49 g, 464.15 mmol) in 670 mL water-free pyridine with constant stirring. The reaction mixture is kept at ambient temperature (20°–23° C.) for two days. Diethyl ether (2.8 L) is added to this reaction mixture and the organic phase is washed six times with water, twice with diluted aqueous sodium carbonate, and then washed with water until neutral. After drying the organic phase over sodium sulfate, the solvent is removed under reduced pressure. The residue is triturated with isopropanol (1140 mL) with stirring until the product crystallizes. After cooling to 4° C., the product, 1-O-octadecyl-2-O-p-toluenesulfonyl-3-O-tritylglycerol, is isolated by filtration, washed with isopropanol and dried under vacuum.

EXAMPLE 9

The procedure of Example 8 is followed except that an equivalent amount of the appropriate 1-O—R-3-O-tritylglycerol is utilized as the starting material of Formula (E) to yield the following respective Formula (F) compounds:
1-O-hexadecyl-2-O-p-toluenesulfonyl-3-O-tritylglycerol,
1-O-eicosyl-2-O-p-toluenesulfonyl-3-O-tritylglycerol,
1-O-tetradecyl-2-O-p-toluenesulfonyl-3-O-tritylglycerol,
1-O-(1-methylheptadecyl)-2-O-p-toluenesulfonyl-3-O-tritylglycerol, and
1-O-(9-cis-octadecenyl)-2-O-p-toluenesulfonyl-3-O-tritylglycerol.

EXAMPLE 10

9-[1'-O-Trityl-3'-octadecyloxypropyl]-adenine:

1-O-Octadecyl-2-O-p-toluenesulfonyl-3-O-tritylglycerol (10.65 g, 14.4 mmol) and adenine (5.8 g, 43 mmol) are dissolved in anhydrous dimethylsulfoxide (100 mL) at 100° C. A solution of dimethylsulfinylmethide, prepared from metallic sodium (0.672 g) in 80 mL anhydrous dimethylsulfoxide, (note: sodium hydride or anhydrous potassium carbonate in dimethylformamide can also be used instead of sodium and dimethylsulfoxide combination), and the resultant reaction mixture is stirred at 100° C. for 72 hours. After cooling, diethyl ether (200 mL) is added. The organic phase is washed six times with water (150 mL each) and dried over sodium sulfate. The solvent is removed under vacuum. The thus obtained crude product is purified by column chromatography and dried under vacuum to afford the product, 9-[1'-O-trityl-3'- octadecyloxypropyl]-adenine.

EXAMPLE 11

The procedure of Example 10 is followed, except that an equivalent amount of the appropriate aminoheterocycle is substituted for the adenine used therein, and reacted with the appropriate 1-O—R-2-O-p-toluenesulfonyl-3-O-tritylglycerol to yield the following respective Formula (G) compounds:
9-[1'-O-trityl-3'-hexadecyloxypropyl]-adenine,
1-[1'-O-trityl-3'-octadecyloxypropyl]-cytosine,
2-amino-1-[1'-O-trityl-3'-octadecyloxypropyl]-imidazole,
3-amino-1-[1'-O-trityl-3'-octadecyloxypropyl]-pyrazole,
3-amino-1-[1'-O-trityl-3'-octadecyloxypropyl]-triazole,
5-fluoro-1-[1'-O-trityl-3'-octadecyloxypropyl]-cytosine
5-bromo-1-[1'-O-trityl-3'-octadecyloxypropyl]-cytosine,
5-amino-1-[1 '-O-trityl-3'-octadecyloxypropyl]-indazole,
2-amino-6-chloro-9-[1'-O-trityl-3'-octadecyloxypropyl]-purine,
9-[1'-O-trityl-3 '-octadecyloxypropyl]-guanine, and
9-[1'-O-trityl-3 '-(9-cis)-octadecenyloxypropyl]-adenine.

EXAMPLE 12

9-[1'-Hydroxy-3'-octadecyloxypropyl]-adenine

A solution of boron trifluoride (50%) in methanol (4 mL) is added to a solution of 9-[1'-O-trityl-3'-octadecyloxypropyl]adenine (4.9 g, 6.9 mmol) in methylene chloride (100 mL) and the resultant dark green solution is kept at ambient temperature for 24 hours. The reaction mixture is then washed with water (30 mL); the color changes to yellow. The resulting emulsion is separated into two phases by the addition of sodium chloride. The organic phase is washed consecutively with diluted aqueous sodium carbonate and water until neutral. After drying over sodium sulfate, the solvent is removed under vacuum. The thus obtained crude 9-[1'-hydroxy-3'-octadecyloxy-propyl]-adenine is purified by column chromatography.

EXAMPLE 13

9-[1'-Hydroxy-3'-octadecylthiopropyl]-adenine

By following the procedure outlined in Example 9, except that an equivalent amount of the appropriate 1-S-alkyl-3-O-tritylthioglycerol is utilized as the starting glycerol derivative to yield the appropriate 1-S-alkyl-2-O-p-toluenesulfonil-3-O-trityl intermediate. Treatment of the intermediate with the appropriate N—Het—NH$_2$, followed by detritylation, as described in steps 2 and 3 of Reaction Scheme 3, the following representative compounds of Formula (J) compounds are obtained:
9-[1'-hydroxy-3'-hexadecylthiopropyl]-adenine,
2-amino-1-[1'-hydroxy-3'-octadecylthiopropyl]-imidazole,
3-amino-1-[1'-hydroxy -3'-octadecylthiopropyl]-pyrazole, 3-amino-1-[1'-hydroxy -3'-octadecylthiopropyl]-triazole,
5-fluoro-1-[1'-hydroxy -3'-octadecylthiopropyl]-cytosine,
5-bromo-1-[1'-hydroxy -3'-octadecylthiopropyl]-cytosine,
5-amino-1-[1'-hydroxy -3'-octadecylthiopropyl]-indazole,
2-amino-6-chloro-9-[1'-hydroxy -3'-octadecylthiopropyl]-purine,
9-[1'-hydroxy-3'-octadecylthiopropyl]-guanine, and
9-[1'-Hydroxy-3'-(9-cis-octadecenylthio)propyl]-adenine.

EXAMPLE 14

9-[1'-O-Trityl-2'-octadecyloxypropyl]1-adenine

Compounds of Formula (L), for example 1-O-p-toluenesulfonyl-2-O-octadecyl-3-O-tritylglycerol, are known in the art. See Brachwitz et al., *J. Prakt. Chem.* (1979) 321:775–786. 1-O-p-Toluenesulfonyl-2-O-octadecyl-3-O-tritylglycerol (10.65 g, 14.4 mmol) and adenine (5.8 g, 43 mmol) are dissolved in anhydrous dimethyl sulfoxide (100 mL) at 100° C. A solution of dimethylsulfinylmethide, prepared from metallic sodium (0.672 g) in 80 ml anhydrous dimethylsulfoxide, is added and the resultant reaction mixture is stirred at 100° C. for 72 hours. After cooling, diethyl ether (200 mL) is added. The organic phase is washed six times with water (150 mL each) and dried over sodium sulfate. The solvent is removed under vacuum. The thus obtained crude product is purified by column chromatography and dried under vacuum to afford the product, 9-[1'-O-trityl-2'-octadecyloxypropyl]-adenine.

EXAMPLE 15

The procedure of Example 14 is followed except that an equivalent amount of the appropriate aminoheterocycle is substituted for the adenine used therein and reacted with the appropriate 1-O-p-toluenesulfonyl-2-O-alkyl-3-O-tritylglycerol to yield the following respective Formula (M) compounds:
9-[1'-O-trityl-2'-hexadecyloxypropyl]-adenine,
1-[1'-O-trityl-2'-octadecyloxypropyl]-cytosine,
2-amino-1-[1'-O-trityl-2'-octadecyloxypropyl]-imidazole,
3-amino-1-[1'-O-trityl-2'-octadecyloxypropyl]-pyrazole,
3-amino-1-[1'-O-trityl-2'-octadecyloxypropyl]-triazole,
5-fluoro-1-[1'-O-trityl-2'-octadecyloxypropyl]-cytosine
5-bromo-1-[1'-O-trityl-2'-octadecyloxypropyl]-cytosine,
5-amino-1-[1-O-trityl-2'-octadecyloxypropyl]-indazole,
2-amino-6-chloro-9-[1'-O-trityl-2'-octadecyloxypropyl]-purine, and
9-[1'-O-trityl-2'-octadecyloxypropyl]-guanine.

EXAMPLE 16

9-[1'-Hydroxy-2'-octadecyloxypropyl]-adenine

A solution of boron trifluoride (50%) in methanol (4 mL) is added to a solution of 9-[1'-O-trityl-2'-octadecyloxypropyl]adenine (4.9 g, 6.9 mmol) in methylene chloride (100 mL) and the resultant dark green solution is kept at ambient temperature for 24 hours. The reaction mixture is then washed with water (30 mL); the color changes to yellow. The resulting emulsion is separated into two phases by the addition of sodium chloride. The organic phase is washed consecutively with diluted aqueous sodium carbonate and water until neutral. After drying over sodium sulfate, the solvent is removed under vacuum. The thus obtained crude 9-[1'-hydroxy-2'-octadecyloxy-propyl]-adenine is purified by column chromatography.

EXAMPLE 17

The procedure for the Example 17 is followed using an equivalent amount of the appropriate compounds of Formula (M), and the following respective Formula (N) compounds are obtained:

9-[1'-hydroxy-2'-hexadecyloxypropyl]-adenine,
1-[1'-hydroxy-2'-octadecyloxypropyl]-cytosine,
2-amino-1-[1'-hydroxy -2'-octadecyloxypropyl]-imidazole,
3-amino-1-[1'-hydroxy -2'-octadecyloxypropyl]-pyrazole,
3-amino-1-[1'-hydroxy -2'-octadecyloxypropyl]-triazole,
5-fluoro-1-[1'-hydroxy -2'-octadecyloxypropyl]-cytosine
5-bromo-1-[1'-hydroxy -2'-octadecyloxypropyl]-cytosine,
5-amino-1-[1-hydroxy -2'-octadecyloxypropyl]-indazole,
2-amino-6-chloro-9-[1'-hydroxy -2'-octadecyloxypropyl]-purine,
9-[1'-hydroxy -2'-octadecyloxypropyl]-guanine, and
9-[ 1'-hydroxy-2'-(9-cis-octadecenyloxy)propyl]-adenine.

EXAMPLE 18

9-[1'-Hydroxy-2'-octadecylthiopropyl]-adenine

9-[1'-O-Trityl-2'-octadecylthiopropyl]adenine is obtained from 1-O-p-toluenesulfonyl-2-S-octadecyl-3-O-tritylglycerol which in turn is obtained from 2-S-octadecyl-3-O-tritylglycerol by Steps 1 and 2 of Reaction Scheme 5.

A solution of boron trifluoride (50%) in methanol (4 mL) is added to a solution of 9-[1'-O-trityl-2'-octadecylthiopropyl]adenine (4.9 g, 6.9 mmol) in methylene chloride (100 mL), and the resultant dark green solution is kept at ambient temperature for 24 hours. The reaction mixture is then washed with water (30 mL); the color changes to yellow. The resulting emulsion is separated into two phases by the addition of sodium chloride. The organic phase is washed consecutively with diluted aqueous sodium carbonate and water until neutral. After drying over sodium sulfate, the solvent is removed under vacuum. The thus obtained crude 9-[1'-hydroxy-2'-octadecylthiopropyl]-adenine is purified by column chromatography.

EXAMPLE 19

By following the procedure outlined in Example 18, except that an equivalent amount of 1-O-p-toluenesulfonyl-2-S—R-3-O-tritylglycerol is treated with the appropriate heterocyclic amine followed by detritylation as described in Step 3 of Reaction Scheme 3, the following representative compounds of Formula (Q) compounds are obtained:
1-[1'-hydroxy-2'-hexadecylthiopropyl]-adenine,
1-[1'-hydroxy-2'-octadecylthiopropyl]-cytosine,
2-amino-1-[1'-hydroxy-2'-octadecylthiopropyl]-imidazole,
3-amino-1-[1'-hydroxy -2'-octadecylthiopropyl]-pyrazole,
3-amino-1-[1'-hydroxy -2'-octadecylthiopropyl]-triazole,
5-fluoro-1-[1'-hydroxy -2'-octadecylthiopropyl]-cytosine,
5-bromo-1-[1'-hydroxy -2'-octadecylthiopropyl]-cytosine,
5-amino-1-[1'-hydroxy -2'-octadecylthiopropyl]-indazole,
2-amino-6-chloro-9-[1'-hydroxy -2'-octadecylthiopropyl]-purine,
9-[1'-hydroxy-2'-octadecylthiopropyl]-guanine, and
9-[1'-hydroxy-2'-(9-cis-octadecenylthio)propyl]-adenine.

EXAMPLE 20

1-[2'-Hydroxy-3'-octadecyloxypropyl]-piperazine 1,2-Epoxy-3-octadecyloxypropane (5.0 g, 15.3 mmol) is added to a mixture of piperazine (1.94 g, 22.5 mmol) and anhydrous potassium carbonate (100 mg) in dimethyl formamide (60 mL) over a 30 minute period under a nitrogen atmosphere. The resultant mixture is stirred at 80°–90° C. (oil bath temperature) for 48 hours. The reaction mixture is cooled to room temperature and concentrated in vacuo to leave a residue. The residue is stirred with chloroform (125 mL). The undissolved material is filtered in vacuo, and the filtrate is concentrated in vacuo, purified by chromatography and dried in vacuo to afford 1-[2'-hydroxy-3'-octadecyloxypropyl]-piperazine.

EXAMPLE 21

The procedure of Example 20 is followed except that an equivalent amount of the appropriate 1,2-epoxy-3-X-R-propane is utilized as the starting Formula (A/C) compound to yield the following respective Formula (Q) compounds:
1-[2'-Hydroxy-3'-octadecylthiopropyl]-piperazine;
1-[2'-Hydroxy-3'-hexadecyloxypropyl]-piperazine;
1-[2'-Hydroxy-3'-hexadecylthiopropyl]-piperazine;
1-[2'-Hydroxy-3'-(9-cis-octadecyloxypropyl]-piperazine; and
15 1-[2'-Hydroxy-3'-(9-cis-octadecyloxypropyl]-piperazine.

EXAMPLE 22

1-N-Amino-4-N-[2'-hydroxy-3'-octadecyloxypropyl]-piperazine

A solution of hydroxylamine-O-sulfonic acid (0.17 g, 1.5 mmol) in 1:1 tetrahydrofuran-water (10 mL) is added dropwise to a mixture of 1-[2'-hydroxy-3'-octadecyloxypropyl]-piperazine (3.0 g, 7.3 mmol) and sodium hydroxide (0.29 g) in 1:1 tetrahydrofuran-water (30 mL) at 15° C. over a 30 minute period under a nitrogen atmosphere. The resultant mixture is stirred at 15° C. for 2 hours. Three additional portions of NaOH (0.29 g each) are then added to the mixture. The reaction mixture is extracted with dichloromethane, dried over NaOH, concentrated and chromatographed to afford 1-N-Amino-4-N-[2'-hydroxy-3'-octadecyloxypropyl]-piperazine.

EXAMPLE 23

The procedure of Example 22 is followed except that an equivalent amount each of the appropriate Formula (Q) compound is utilized as the initial reactant to yield the following respective Formula (B/D) compounds as final products:
1-N-amino-4-[2'-Hydroxy-3'-octadecylthiopropyl]-piperazine;
1-N-amino-4-[2'-Hydroxy-3'-hexadecyloxypropyl]-piperazine;
1-N-amino-4-[2'-Hydroxy-3'-hexadecylthiopropyl]-piperazine;
1-N-amino-4-[2'-Hydroxy-3'-(9-cis-octadecyloxypropyl]-piperazine; and
1-N-amino-4-[2'-Hydroxy-3'-(9-cis-octadecyloxypropyl]-piperazine.

EXAMPLE 24

This is an illustrative example of tablets containing the following ingredients which may be prepared in a conventional manner:

| Ingredients | Per Tablet (mg) |
| --- | --- |
| CPR1148 | 50–100 |
| Lactose | 70 |
| Maize starch | 70 |
| Polyvinylpyrrolidine | 5 |
| Magnesium Stearate | 5 |
| Tablet weight | 200–250 |

EXAMPLE 25

An illustrative oil-in-water cream base formulation for topical use which may be prepared in a conventional manner:

| Ingredients | Grams |
| --- | --- |
| CPR1149 | 10.0 |
| Anhydrous lanolin | 20.0 |
| Polysorbate | 4.0 |
| Sorbitan monopalmitate | 2.0 |
| Light liquid paraffin | 4.0 |
| Propylene glycol | 5.0 |
| Methyl hydroxybenzoate | 0.1 |
| Purified water, to | 100.0 |

EXAMPLE 26

An illustrative example of a water-soluble gel containing the following ingredients which may be prepared in a conventional manner:

| Ingredients | Per Packet (mg) |
| --- | --- |
| CPR1148 | 195 |
| Carbomer 934P | 400 |
| Propylene glycol | 400 |
| Purified water, to | 2900 |
| Total weight | 3895 |

EXAMPLE 27

An illustrative example of a water-insoluble ointment containing the following ingredients which may be prepared in a conventional manner:

| Ingredients | Per Tube (g) |
| --- | --- |
| CPR1152 | 1.0 |
| Lactose | 2.0 |
| Mineral Oil | 11.0 |
| Polyethylene | 6.0 |
| Total weight | 20.0 |

EXAMPLE 28

An illustrative example of a lotion containing the following ingredients which may be prepared in a conventional manner:

| Ingredients | Per Bottle |
| --- | --- |
| CPR1152 | 1.425 mg |
| Cetyl Alcohol | 2 mL |
| Steric Acid | 2 mL |
| Glycerin | 15 mL |
| Triethanolamine | 4 mL |
| Purified Water, to | 24 mL |
| Bottle volume | 57 mL |

EXAMPLE 29

An illustrative example of pharmaceutical appliances for topical application to a wound site.

A solution is made consisting of 5.0% by weight of CPR 1152 in phosphate buffered saline (pH 6.8). A conventional gauze pad, for example, 3 in. by 3 in., and a conventional surgical cellulosic sponge are submerged into the solution until saturated. Each thoroughly solution impregnated item is removed from the solution, dried, packaged and sterilized for use when needed.

We claim:

1. An aminoheterocycle-substituted glycerol having the Formula I:

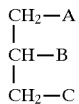
      I wherein:
- one of A, B or C is —X—R, wherein X is oxygen or sulfur and R is a substituted or unsubstituted, linear or branched-chain $C_{12-24}$ alkyl or alkenyl, the substituent being one or more of halo, $C_{1-3}$ alkoxy or cyano, provided that a double bond of the alkenyl does not originate at a carbon atom bound to X;
- another of A, B, or C is a substituted or unsubstituted aminoheterocycle —Het—$NH_2$, wherein Het is a 5 to 11-membered monocyclic, bicyclic or bicyclic fused heterocyclic ring moiety with at least 1 to 4 nitrogen atoms contained within the heterocycle moiety, one of which nitrogen atoms is bonded to a glycero carbon, and wherein when substituted the heterocycle moiety is substituted with one or more substituents selected from the group consisting of $C_{1-3}$ alkyl, $C_{1-3}$ alkoxy, fluoro, cyano, nitro, methylsulfono, and exocyclic carbonyl (=O); and
- another of A, B or C is hydroxy;
- and further provided that A, B and C are each different; isomers thereof; or pharmaceutically-acceptable salts thereof.

2. A compound of claim 1 selected from the group consisting of:
9-(2'-hydroxy-3'-octadecyloxypropyl)-adenine;
1-(2'-hydroxy-3'-octadecyloxypropyl)-cytosine; and
5-fluoro-1-(2'-hydroxy-3'-octadecyloxypropyl)-cytosine.

3. A compound of claim 1 wherein said —Het—$NH_2$ is selected from the group consisting of: 2-aminoimidazolyl; 3-aminopyrazolyl; 3-aminotriazolyl; 5-bromocytosinyl; 5-aminoindazolyl; 2-amino-6-chloropurinyl; and 9-guaninyl.

4. A method of treating wounds in a mammal afflicted with damaged tissue cells which comprises administering to the mammal an amount of an aminoheterocycle-substituted glycerol as recited in claim 1, the amount being effective to promote healing of the damaged tissue cells.

5. The method of claim 4 wherein a compound selected from the group consisting of:
9-(2'-hydroxy-3'octadecyloxypropyl)-adenine;
1-(2'-hydroxy-3'-octadecyloxypropyl)-cytosine; and
5-fluoro-1-(2'-hydroxy-3'-octadecyloxypropyl)-cytosine is administered to the mammal.

6. The method of claim 4 wherein a compound where —Het—$NH_2$ is selected from the group consisting of: 2-aminoimidazolyl; 3-aminopyrazolyl; 3-aminotriazolyl; 5-bromocytosinyl; 5-aminoindazolyl; 2-amino-6-chloropurinyl; and 9-guaninyl is administered to the mammal.

7. A pharmaceutical composition comprising an effective tissue cell growth-promoting amount of an aminoheterocycle-substituted glycerol as recited in claim 1 in combination with a pharmaceutically-acceptable carrier.

8. The pharmaceutical composition of claim 7 comprising a compound selected from the group consisting of:
9-(2'-hydroxy-3'octadecyloxypropyl)-adenine;
1-(2'-hydroxy-3'-octadecyloxypropyl)-cytosine; and
5-fluoro-1-(2'-hydroxy-3'-octadecyloxypropyl)-cytosine.

9. The pharmaceutical composition of claim 7 comprising a compound wherein —Het—$NH_2$ is selected from the group consisting of: 2-aminoimidazolyl; 3-aminopyrazolyl; 3-aminotriazolyl; 5-bromocytosinyl; 5-aminoindazolyl; 2-amino-6-chloropurinyl; and 9-guaninyl.

* * * * *